(12) United States Patent
Mastrototaro et al.

(10) Patent No.: US 7,417,191 B2
(45) Date of Patent: Aug. 26, 2008

(54) TEST PLUG AND CABLE FOR A GLUCOSE MONITOR

(75) Inventors: John J. Mastrototaro, Los Angeles, CA (US); Richard E. Purvis, Pasadena, CA (US); Edgardo C. Halili, Valencia, CA (US); Eric Johnson, Sherman Oaks, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 0 days.

(21) Appl. No.: 11/637,295

(22) Filed: Dec. 12, 2006

(65) Prior Publication Data

US 2007/0087633 A1    Apr. 19, 2007

Related U.S. Application Data

(62) Division of application No. 10/153,098, filed on May 22, 2002, now Pat. No. 7,150,655, which is a division of application No. 09/511,819, filed on Feb. 24, 2000, now Pat. No. 6,418,332.

(60) Provisional application No. 60/121,656, filed on Feb. 25, 1999.

(51) Int. Cl.
    *H01B 9/02* (2006.01)
(52) U.S. Cl. ............................. 174/105 R; 174/128.1
(58) Field of Classification Search ............. 174/105 R, 174/128.1, 128.2
    See application file for complete search history.

(56) References Cited

U.S. PATENT DOCUMENTS 4,327,246 A    4/1982    Kincaid (Continued)

FOREIGN PATENT DOCUMENTS

DE    19706753    8/1997

(Continued)

OTHER PUBLICATIONS

U.S. Appl. No. 09/377,472, filed Aug. 19, 1999 (now abandoned).

(Continued)

*Primary Examiner*—Chau N Nguyen
(74) *Attorney, Agent, or Firm*—Gates & Cooper LLP

(57) ABSTRACT

Methods and apparatuses for electrically connecting a medical glucose monitor to a glucose sensor set, as well as for testing the operation of the glucose monitor, monitor cable and glucose sensor set are provided. In one embodiment, an electric cable comprises a cable member, a first connector and a second connector. The cable member in turn comprises at least one insulated conductor, a conductive shielding layer disposed around the at least one insulated conductor; and an insulating layer disposed around the conductive shielding layer. A glucose monitoring system test plug provides for a releasable electrical connection with the electric cable. In one embodiment, the test plug comprises a housing and a fitting affixed thereto which is adapted to electrically couple the test plug with the electric cable. The test plug further includes an electrical circuit that produces a signal that is read by the glucose monitor to test the operational performance of the glucose monitor and the electric cable when the test plug is coupled to the electric cable and when the electric cable is coupled to the glucose monitor.

4 Claims, 7 Drawing Sheets

U.S. PATENT DOCUMENTS

| | | |
|---|---|---|
| 4,385,272 A | 5/1983 | Whitehead |
| 4,498,479 A | 2/1985 | Martio et al. |
| 4,510,346 A | 4/1985 | Bursh, Jr. et al. |
| 4,573,994 A | 3/1986 | Fischell et al. |
| 4,676,568 A | 6/1987 | Nault et al. |
| 4,760,730 A | 8/1988 | Frank et al. |
| 4,857,857 A | 8/1989 | Valenti et al. |
| 5,107,076 A | 4/1992 | Bullock et al. |
| 5,124,661 A | 6/1992 | Zelin et al. |
| 5,233,986 A | 8/1993 | Robson |
| 5,390,671 A | 2/1995 | Lord et al. |
| 5,391,250 A | 2/1995 | Cheney, II et al. |
| 5,414,213 A | 5/1995 | Hillburn |
| 5,482,473 A | 1/1996 | Lord et al. |
| 5,523,534 A | 6/1996 | Meister et al. |
| 5,557,210 A | 9/1996 | Cappa et al. |
| 5,586,553 A | 12/1996 | Halili et al. |
| 5,683,270 A | 11/1997 | Warislohner |
| 5,781,024 A | 7/1998 | Blomberg et al. |
| 5,792,068 A | 8/1998 | Bowman et al. |
| 5,824,959 A | 10/1998 | Mista et al. |
| 5,834,699 A | 11/1998 | Buck et al. |
| 5,954,643 A | 9/1999 | VanAntwerp et al. |
| 6,030,346 A | 2/2000 | Buck et al. |
| 6,038,481 A | 3/2000 | Werner et al. |
| 6,113,537 A | 9/2000 | Castano |
| 6,117,083 A | 9/2000 | Buck et al. |
| 6,368,141 B1 | 4/2002 | VanAntwerp et al. |
| 6,418,332 B1 | 7/2002 | Mastrototaro et al. |

FOREIGN PATENT DOCUMENTS

| | | |
|---|---|---|
| WO | 96/25088 | 8/1996 |
| WO | 96/35370 | 11/1996 |
| WO | 98/56078 | 12/1998 |
| WO | 98/56293 | 12/1998 |

OTHER PUBLICATIONS

PCT/US00/04854 International Search Report mailed Jul. 5, 2000.
PCT/US00/04854 Supplemental International search Report mailed Oct. 16, 2000.

TEST PLUG AND CABLE FOR A GLUCOSE MONITOR

RELATED APPLICATIONS

This application claims priority on U.S. Provisional Patent Application No. 60/121,656, filed Feb. 25, 1999 and which is incorporated herein by reference.

BACKGROUND OF THE INVENTION

1. Field of the Invention

This invention relates to methods and devices used for electrically connecting medical glucose monitors to glucose sensor electrodes as well as for testing the operation of the glucose monitors, monitor cables and glucose sensors.

2. Description of the Related Art

Over the years, a variety of implantable electrochemical sensors have been developed for detecting or quantifying specific agents or compositions in a patient's blood. For instance, glucose sensors are being developed for use in obtaining an indication of blood glucose levels in a diabetic patient. Such readings are useful in monitoring or adjusting a treatment regimen which typically includes the regular administration of insulin to the patient. Thus, blood glucose readings can improve medical therapies with semi-automated medication infusion pumps of the external type, as generally described in U.S. Pat. Nos. 4,562,751; 4,678,408; and 4,685,903; or automated implantable medication infusion pumps, as generally described in U.S. Pat. No. 4,573,994, which are incorporated herein by reference.

Generally, small and flexible electrochemical sensors can be used to obtain periodic readings over an extended period of time. In one form, flexible subcutaneous sensors are constructed in accordance with thin film mask techniques in which an elongated sensor includes thin film conductive elements encased between flexible insulative layers of polyimide sheets or similar material. Such thin film sensors typically include a plurality of exposed electrodes at one end for subcutaneous placement with a user's interstitial fluid, blood, or the like, and a corresponding exposed plurality of conductive contacts at another end for convenient external electrical connection with a suitable monitoring device through a wire or cable. Typical thin film sensors are described in commonly assigned U.S. Pat. Nos. 5,390,671; 5,391,250; 5,482,473; and 5,586,553 which are incorporated herein by reference.

Thin film sensors generate very small electrical signals which can be read by external glucose monitors. These monitors can be portable, and can be attached to the patient, such as for example, on a belt clip. Applicant's clinical studies have shown that an electrical cable may be provided for the transmission of these small signals from the sensors to the glucose monitor. But given the environment in which these cables are used, special characteristics can be useful.

Thus a glucose monitoring system includes connectors between the cables, leads, electrodes and monitors such as those described in pending U.S. patent application Ser. No. 09/346,835, filed Jul. 2, 1999 and entitled "Insertion Set for a Transcutaneous Sensor" and U.S. patent application Ser. No. 09/377,472, filed Aug. 19, 1999 and entitled "Telemetered Characteristic Monitor System and Method of Using Same, both of which are incorporated herein by reference. Although a well designed system will have minimal operational problems, it is possible that a problem might arise with the integrity of the cables, sensor electrodes or monitor during their use. The system connectors or the cables may become loose or bent, resulting in a poor or open circuit. The sensor electrodes could degrade. The glucose monitor could become inoperative due to any number of causes. Thus, it is desirable to provide a system that is simple to use so that a patient can easily identify any operational problems with the system.

SUMMARY OF THE PREFERRED EMBODIMENTS

A glucose monitoring system test plug as well as an electric cable for electrically connecting a glucose monitor to a glucose sensor set are provided. In one embodiment, the electric cable comprises a cable member, a first connector and a second connector. The cable member in turn comprises at least one insulated conductor, a conductive shielding layer disposed around the at least one insulated conductor; and an insulating layer disposed around the conductive shielding layer.

In one aspect, the first connector comprises a housing having a first bore which is adapted to receive a sensor set cable fitting and a first conductive contact disposed within the first bore. The first conductive contact is electrically coupled to the insulated conductor and is adapted to be removably electrically coupled to a sensor set conductive contact. In one embodiment of the present invention, a key fitting is formed within the first bore and is adapted to mate with the glucose sensor set in one orientation. There is further provided a releasable coupler disposed on the housing which is adapted to releasably couple the housing with the glucose sensor set.

In another aspect, the second connector comprises a housing having a second bore. The second connector is adapted to releasably couple the second connector with the glucose monitor. There is a second conductive contact disposed within the second bore which is electrically coupled to the insulated conductor. The second conductive contact also is adapted to be removably electrically coupled to a glucose monitor conductive contact.

In yet another aspect, the glucose monitoring system test plug is for use with a glucose monitor cable which is adapted to electrically couple to a glucose monitor. The test plug comprises a housing and a fitting affixed to the housing. The fitting is adapted to electrically couple the test plug to the glucose monitor cable. The test plug further comprises an electrical circuit which is adapted to provide a known test signal to the cable and the glucose monitor in order to test the operational performance of the glucose monitor and the glucose monitor cable when the test plug is coupled to the glucose monitor cable and when the glucose monitor cable is coupled to the glucose monitor.

In an alternative embodiment, the test plug is provided for use with a glucose monitor. The test plug comprises a housing and a fitting affixed to the housing. The fitting is adapted to electrically couple the test plug to the glucose monitor. The test plug further comprises an electrical circuit which is adapted to provide a test signal to the glucose monitor to test the operational performance of the glucose monitor when the test plug is coupled to the glucose monitor.

In yet another embodiment, the test plug can alternatively provide a releasable electrical connection with either the electrical cable or the glucose monitor.

DETAILED DESCRIPTION OF THE PREFERRED EMBODIMENTS

In the following description, reference is made to the accompanying drawings which form a part hereof and which illustrate several embodiments of the present invention. It is understood that other embodiments may be utilized and structural and operational changes may be made without departing from the scope of the present invention.

Figure 1:
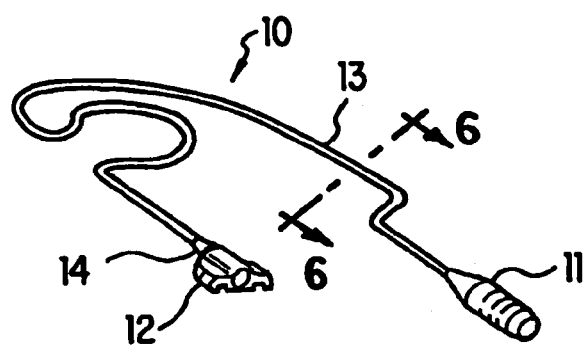
FIG. 1 is a perspective view of an electrical cable for a glucose monitor in accordance with one embodiment of the inventions.
Figure 2:
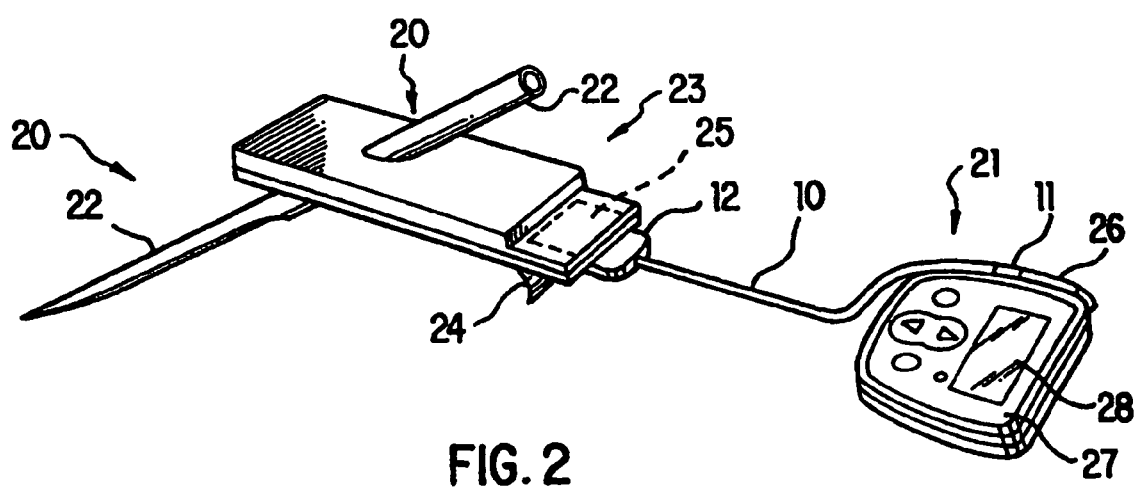
FIG. 2 is a perspective view of a glucose monitoring system using the cable of FIG. 1.

Referring to FIG. 1 there is disclosed a shielded cable 10 constructed in accordance with aspects of the present invention. The cable 10 includes a flexible cable member 13 with a monitor connector 11 at one end and a sensor connector 12 at the opposite end. FIG. 2 illustrates the use of the cable 10 in an exemplary glucose monitoring system. The system includes a subcutaneous glucose sensor set 20 which is coupled to a glucose monitor 21 by the cable 10. The subcutaneous glucose sensor set 20 uses an electrode-type sensor, as described in more detail below. However, in other applications, the glucose sensor may use other types of sensors, such as chemical based, optical based or the like. The sensor shown in FIG. 2 is a surface mounted sensor that uses interstitial fluid harvested from the skin. Other sensors may be of a type that is used on the external surface of the skin or placed below the skin layer of the user.

The glucose monitor 21 of the illustrated embodiment generally includes the capability to record and store data as it is received from the sensor set 20, and includes either a data port or a wireless transmitter for downloading the data to a data processor, computer, communication station, or the like for later analysis and review. The data processor or computer uses the recorded data from the glucose monitor to determine the blood glucose history. Thus, one purpose of the glucose monitor system is to provide for improved data recording and testing for various patient conditions using continuous or near continuous data recording.

The sensor set 20 of the illustrated embodiment is provided for subcutaneous placement of a flexible sensor, or the like, at a selected site in the body of the user. The sensor set 20 includes a hollow, slotted insertion needle 22 and a cannula (not shown) inside the needle 22. The needle 22 is used to facilitate quick and easy subcutaneous placement of the cannula at the insertion site. The cannula includes one or more sensor electrodes (not shown) which are exposed to the user's bodily fluids. After insertion, the insertion needle 22 is typically withdrawn to leave the cannula with the sensor electrodes in place at the selected insertion site.

The sensor set 20 includes a mounting base 23 adapted for placement onto the skin of a user. As shown, the mounting base 23 of the illustrated embodiment is a generally rectangular pad having an underside surface coated with a suitable pressure sensitive adhesive layer, with a peel-off paper strip 24 provided to cover and protect the adhesive layer, until the sensor set 20 is ready for use. Further description of suitable needles and sensor sets are found in U.S. Pat. No. 5,586,553, entitled "Transcutaneous Sensor Insertion Set" and U.S. patent application Ser. No. 09/346,835, filed Jul. 2, 1999, entitled "Insertion Set for a Transcutaneous Sensor," which are incorporated herein by reference.

Figure 3:
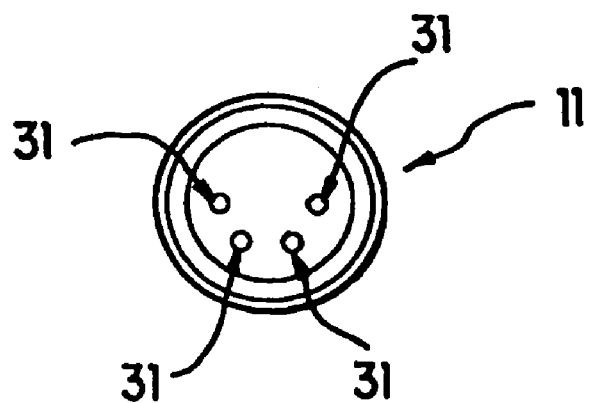
FIG. 3 is an end plan view of a glucose monitor connector portion of the glucose monitor cable of FIG. 1.

As shown in FIGS. 2 and 3, the glucose monitor 21 is coupled to the sensor set 20 by the cable 10 which electrically couples the monitor connector 11 to the connector block 25 of the sensor set 20. The monitor connector 11 of the cable 10 is connected to the glucose monitor 21 through a plug receptacle 26 of the monitor 21. The monitor connector 11 includes a plurality of pins 31 arranged in a pin snap-in configuration to connect to the receptacle 26 of the glucose monitor 21. In this embodiment, there are four (4) pins 31, three (3) of which are used for connection to 3 insulated conductors within the cable 10 and one of which is for a drain (or ground) conductor within the cable 10.

The glucose monitor 21 includes a housing 27 that supports at least one printed circuit board, batteries, memory storage, a display screen 28, the plug receptacle 26, and the cable 10 and the monitor connector 11 when connected to the plug receptacle 26 of the monitor 21. The lower portion of the glucose monitor 21 may have an underside surface that includes a belt clip, or the like, to attach to a user's clothing. Alternatively, the underside surface may be coated with a suitable pressure sensitive adhesive layer, with a peel-off paper strip normally provided to cover and protect the adhesive layer until the glucose monitor 21 is ready for use. Alternatively, the glucose monitor 21 may be secured to the body by other methods, such as an adhesive overdressing, straps, belts, clips, or the like. Further description of suitable glucose monitors are found in U.S. patent application Ser. No. 09/377,472, entitled "Telemetered Characteristic Monitor System and Method of Using the Same" which is incorporated herein by reference.

In other embodiments, the cable 10 may also have a flexible strain relief portion, as indicated at reference numeral 14 of FIG. 1, to minimize strain on the sensor set 20 and minimize movement of the sensor set 20 relative to the body, which can lead to discomfort or dislodging of the sensor set 20. The flexible strain relief portion is intended to also minimize sensor artifacts generated by user movements that causes the sensor set 20 to move laterally relative to the glucose monitor 21 by reducing lateral movement of the sensor connector 12.

The glucose monitor 21 provides power or other signals, through the plug receptacle 26 to the monitor connector 11 of the cable 10 and then through the cable 10 to the sensor connector 12 of the sensor set 20. These signals are used to drive the sensor electrodes and to speed the initialization of the sensor set 20, when first placed on the skin.

Figure 4:
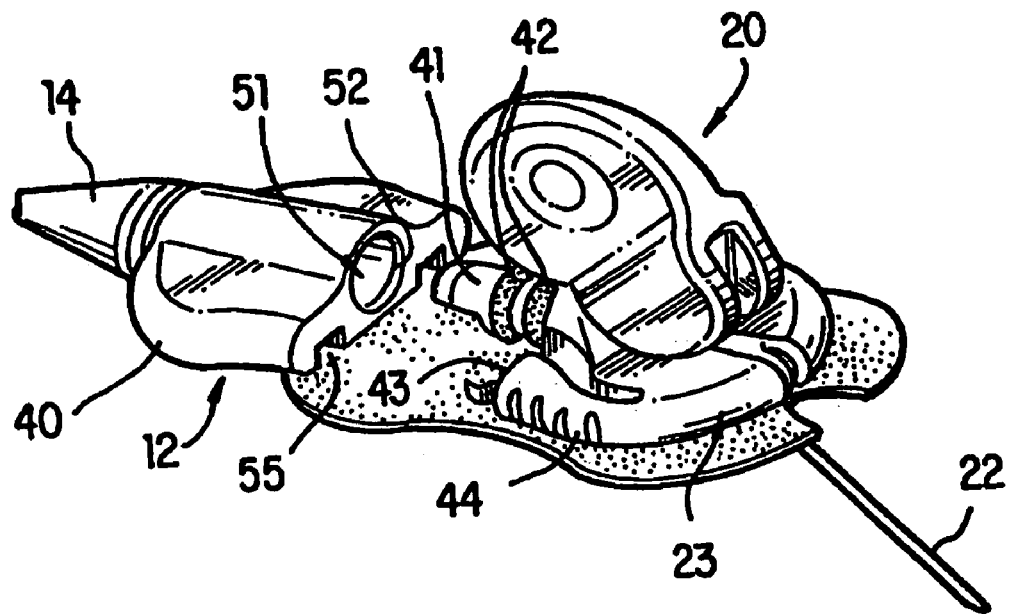
FIG. 4 is a perspective view illustrating the assembly of the glucose monitor cable of FIG. 1 with an insertion set.
Figure 5:
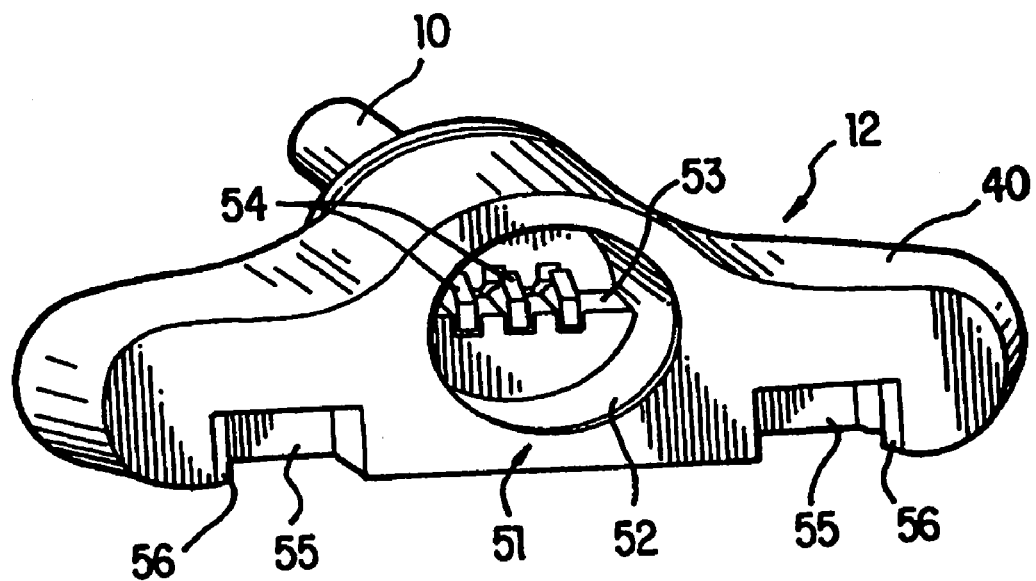
FIG. 5 is a front-end perspective view of a sensor set connector portion of the glucose monitor cable of FIG. 1.

FIGS. 4 and 5 illustrate a connection arrangement between the sensor connector 12 portion of the cable 10 of the illustrated embodiment and the sensor set 20. As shown, the sensor connector 12 has a low profile housing 40 for comfortable fitting against the body. The housing 40 is compact in size and can be constructed from lightweight molded plastic. The housing 40 defines a socket fitting 51 for mating slide-fit engagement with a rear cable fitting 41 of a sensor set mounting base 23. The socket fitting 51 of the illustrated embodiment has a bore or cylindrical entry portion 52 which leads to a generally D-shaped or half-circle step portion 53 positioned within the entry portion 52. The socket fitting 51 therefore forms a "keyhole" type fitting which is sized to receive the D-shaped "key" portion of the sensor set fitting 41.

The socket fitting 51 includes a plurality of conductive contacts 54 (FIG. 5) positioned on the step portion 53 for electrically coupled engagement with correspondingly positioned contact pads of the cable fitting 41, when the sensor set 20 and the sensor connector 12 are coupled together. The conductive contacts 54 of the illustrated embodiment have a leaf spring design to facilitate good electrical and mechanical contact to the sensor set fitting contact pads. When assembled, seal rings 42 of the sensor set fitting 41 sealingly engage the entry portion 52 of the socket fitting 51 to provide a water resistant connection between the components. Furthermore, the D-shaped geometry of the interfitting components 41 and 53 facilitate proper conductive coupling of the cable 10 to the sensor set 20 in the desired orientation.

The sensor set 20 and the sensor connector 12 are held together by releasable couplers, which in the embodiment of FIGS. 4 and 5, include interengaging snap fit latch arms 44 of the sensor set 20 and latch recesses 55 of the connector 12 of the cable 10. As shown, the insertion set mounting base 23 is formed to include the pair of rearwardly projecting cantilevered latch arms 44 which terminate at the rearward ends thereof in respective undercut latch tips 43. The latch arms 44 are sufficiently and naturally resilient to provide a living hinge for movement relative to the remainder of the mounting base 23 to permit the latch arms 44 to be squeezed inwardly toward each other.

The permissible range of motion accommodates snap fit engagement of the latch tips 43 into a corresponding pair of latch recesses 55 formed in the housing 40 of the sensor connector 12 on opposite sides of the socket fitting 51, wherein the latch recesses 55 are lined with indentations which act as latch keepers 56 for engaging the latch tips 43. The components can be disengaged for uncoupling when desired by manually squeezing the latch arms 44 inwardly toward each other for release from the latch keepers 56, while axially separating the mounting base 23 from the sensor connector 12.

For use as a connector between a sensor set and a glucose monitor, the cable 10 includes one or more insulated conductors, and in order to increase user comfort, should be relatively long and have good flexibility. However, the electrical signals from the sensor set 20 electrodes can be very small (i.e., in the range of 1 to 200 nano amps) thus making the cable susceptible to external electrical noise. To reduce this susceptibility the cable is preferably shielded and relatively short. These characteristics would tend in general to make a cable less comfortable for a user.

A further source of electrical noise in cables is the triboelectric effect which is caused by the use of certain electrical insulators. Certain types of insulators, such as for example, Teflon, can be so effective that when the cable is bent, the electrical charge on the cable will separate but will not reform quickly. When the charge belatedly reforms, this can appear as a voltage spike or noise on the cable. Thus, while an effective insulator is useful for glucose monitor cables, the insulator preferably should not permit unacceptable levels of triboelectric noise. Certain insulation materials may provide a good solution to the triboelectric effect. However, many of them would not result in as flexible a cable as is desired.

Figure 6:
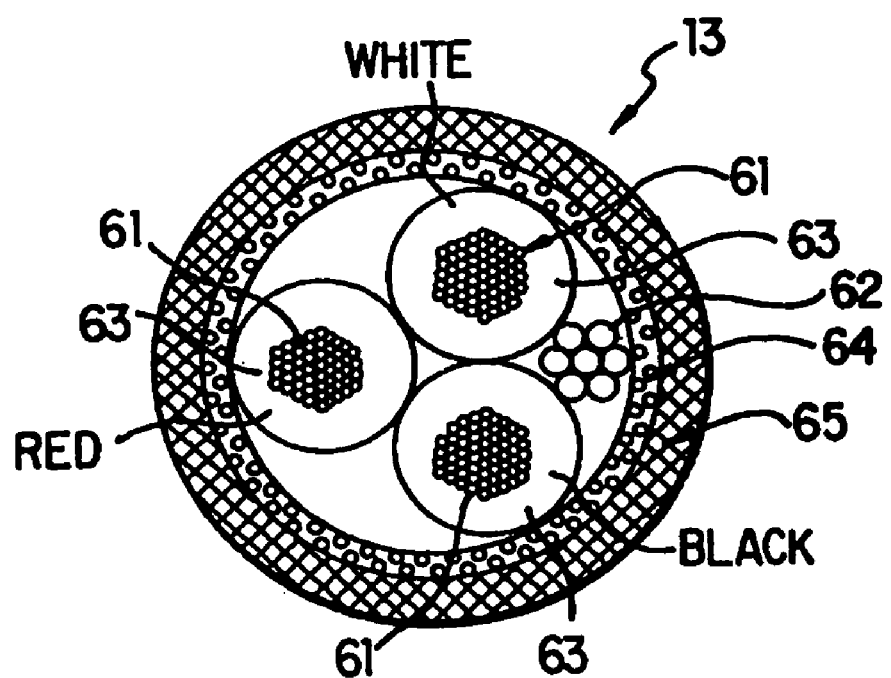
FIG. 6 is a cross-sectional view of a cable member portion of the glucose monitor cable of FIG. 1 as viewed along the lines 6-6 of FIG. 1.

FIG. 6 shows a cross sectional view of an exemplary embodiment of the flexible cable member 13 of the glucose monitor cable 10. This design strikes a satisfactory balance between cable flexibility, high insulation, and low noise characteristics. The cable member 13 includes three (3) center conductors 61 as well as a drain line 62. The center conductors 61 are electrically coupled to the conductive contacts 54 (FIG. 5) of the sensor connector 12 at one end and are coupled to 3 of the 4 pins 31 of the monitor connector 11 at the opposite end. (FIG. 3) The drain line 62 is electrically coupled to the remaining one of the pins 31 of the monitor connector 11 which is electrically grounded. In this embodiment, the center conductors 61 each are constructed of 30 AWG 40×46 BC bunched stranded copper with a nominal OD of 0.013 inches. It is believed that alternative constructions for the conductors 61 may achieve acceptable flexibility if gauges of a number greater than 30 and strand counts greater than 40 are employed. The drain line 62 is constructed of 30 AWG 7×0.004 TC concentric stranded copper with a nominal OD of 0.012 inches. Other gauges, strand counts and OD's for the conductors 61 and the drain line 62 may be used, however depending upon the application.

The three conductors 61 are each surrounded by a first insulating jacket 63, which in the illustrated embodiment is 8 mils nominal PVC insulation with a nominal OD of 0.026 inches. An alternative insulation material to PVC is believed to be a polyester material, such as Mil-ene™ which is available from W. L. Gore & Associates of Newark, Del. The drain line 62 of the illustrated embodiment is not surrounded by a first insulating jacket.

The three conductors 61, their insulating jackets 63 and the drain line 62 are collectively surrounded by a shield 64. The shield 64 is constructed of 44 AWG tinned copper braid with a nominal thickness of 0.007 inches. Other thicknesses and gauges may be used however, depending upon the particular application. The shield 64 serves to prevent or minimize external electromagnetic interference fields from affecting the low level signals being transmitted on the conductors 61. The drain line 62 is adjacent to and therefore in electrical contact with the shield 64 throughout the length of the cable member 13. Because the drain line 62 is electrically coupled to the one of the pins 31 which is grounded, this serves to ground the shield 64. By grounding the shield 64 in this manner, a separate electrical termination of the shield to any sort of alternative grounding on the monitor connector 11 of the cable 10 may be eliminated.

The shield 64 is surrounded by a second insulating jacket 65. The second insulating jacket 65 of the illustrated embodiment is constructed of PVC (USP class VI) which is a "food grade" PVC and has a nominal thickness of 0.010 inch. Alternative acceptable materials to PVC are believed to include thermoplastic elastomers such as Santoprene™ which is available from Advanced Elastomers (a division of Monsanto) of Akron, Ohio, or a reinforced elastomer based material, Sil-Kore™, which is available from W. L. Gore & Associates of Newark, Del. The OD of the insulating jacket 65, and therefore of the cable 10, is approximately 0.090 inches. Although the illustrated embodiment of the outer jacket 65 has a nominal thickness of 0.010 inches and an OD of 0.090, inches, it is believed that nominal thicknesses of 0.006 inches or greater and OD's of 0.110 inches or less may be employed and achieve acceptable results.

When constructed in accordance with the previously-described embodiment, it is believed that the cable 10 will have triboelectric noise characteristics of no more than approximately 50 to 150 micro volts per AAMI ECG 5/83 test. This construction results in a cable member 13 which strikes a satisfactory balance between maximum insulation and minimal triboelectric noise. Moreover, the cable 10 is small in diameter and relatively long and flexible, thus providing a greater degree of user comfort. However, these embodiments may also be used for shorter cables used to connect various components in telemetered systems, such as that described in U.S. patent application Ser. No. 09/377,472 and entitled "Telemetered Characteristic Monitor System and Method of Using Same."

Figure 7:
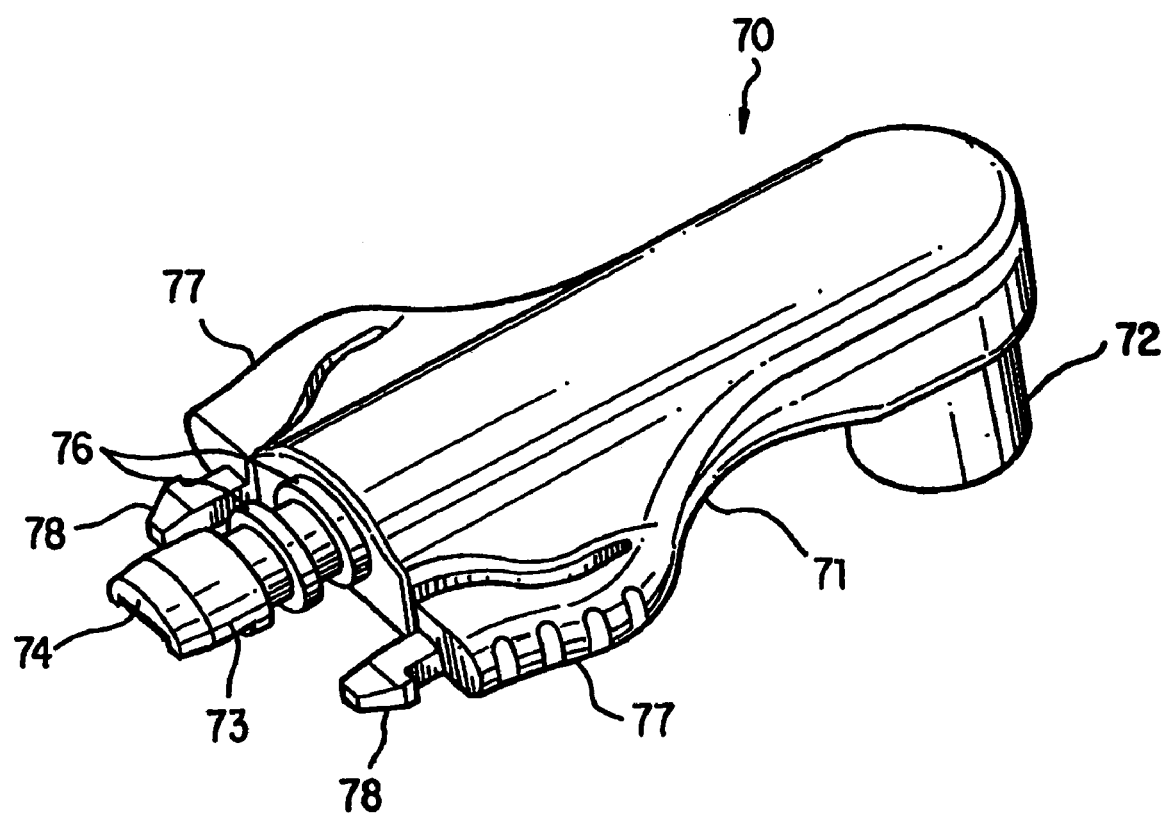
FIG. 7 is a top perspective view of a glucose monitoring system test plug in accordance with another embodiment of the present inventions.

Referring now to FIG. 7, a test plug 70 is disclosed that can simulate the glucose sensor electrodes, or the combination of the glucose sensor electrodes and the cable 10 of a glucose monitoring system. If an operating problem occurs while the glucose monitoring system is being used, the test plug 70 provides diagnostic information that can help indicate if a glucose sensor, the cable or the glucose monitor is operating normally.

The test plug 70 includes two connectors. Each connector facilitates the testing of a different component of a glucose monitoring system. A monitor connector 72 allows the device to plug into the glucose monitor 21 in place of the cable 10 so the monitor can be checked independently from the rest of the system. A cable fitting 73 allows the device to plug into the cable 10 in place of the sensor set 20 so that the operation of the cable 10 can also be verified.

As will be described in more detail below, the test plug 70 is a sensor simulator that, in one embodiment, can return a constant current of the same magnitude as is produced by the sensor electrodes during normal in-vivo operation. This current is measured by the monitor 21 and is reported on the display screen 28 of the monitor 21. (FIG. 2) From the display screen 28, the user can view the test current and verify that the monitor is reporting the correct signal current with the expected accuracy. This can be accomplished when the test plug 70 is plugged directly into the monitor or when it is plugged into the distal end of the cable 10.

The ability to perform such simple performance checks in the field is expected to offer users the opportunity to troubleshoot system problems with greater ease and confidence.

Figure 10:
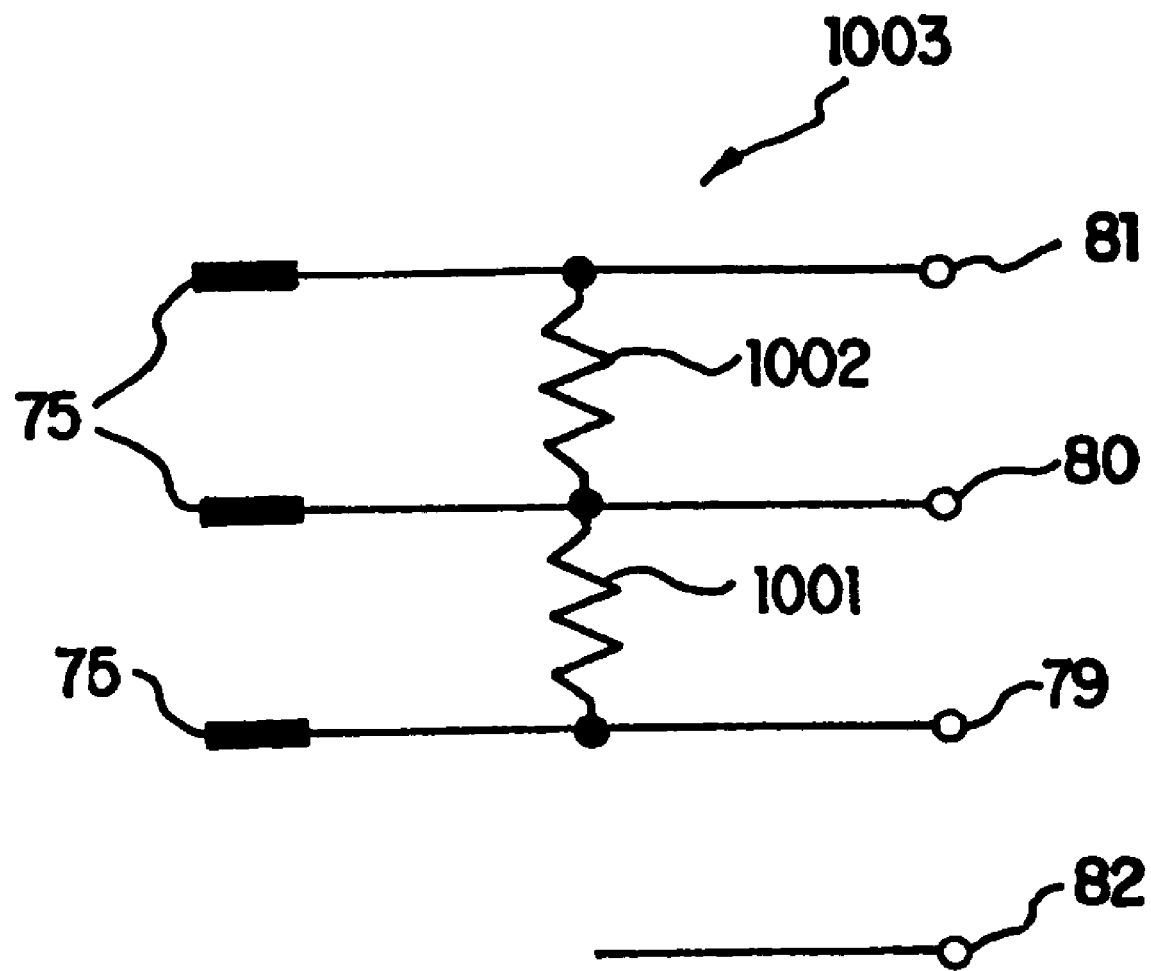
FIG. 10 is a schematic diagram of an electrical circuit used in the glucose monitoring system test plug of FIG. 7.

Referring to FIG. 10, the test plug simulates the presence of an actual sensor electrode to produce a signal current that the monitor can measure. Monitor connector pins 79-82 are disposed in the monitor connector 72 portion of the test plug 70 (FIG. 7) and are adapted for direct connection to the plug receptacle 26 of the glucose monitor 21. (FIG. 2) In one embodiment, the simulator has an electrical circuit 1003 that includes a first resistor 1001 connected between the monitor connector pin 80 which simulates a reference electrode connection and the monitor connector pin 79 which simulates a working electrode connection. The test current produced depends upon the voltage provided by the monitor 21 and the value of the resistor between the simulated reference and working electrode connections. In one embodiment, a test current of 27 nA is developed with a nominal monitor voltage of 535 mV where the first resistor 1001 is 20 million ohms.

A second resistor 1002 is placed between the monitor connector pin 81 which simulates a counter electrode connection and the monitor connector pin 80. The second resistor 1002 is chosen to be of equal value, or 20 million ohms, so that the voltage at the simulated counter electrode 81 will be twice that of the monitor voltage as measured between simulated electrodes 79 and 80. Choosing the second resistor value to produce a voltage twice that of the monitor voltage facilitates verifying the monitor voltage value. Monitor connector pin 82 simulates a connection to the cable drain line 62 (FIG. 6) and therefore is electrically isolated from the resistors 1001 and 1002.

Still referring to FIG. 10, a plurality of contact pads 75 are disposed in the cable fitting 73 portion of the test plug 70 (FIG. 7) and are adapted for electrical connection to the sensor connector 12 of the cable 10. (FIG. 5) When connected to the cable 10, the test plug 70 continues to simulate the presence of an actual sensor electrode. However, it produces a signal current that travels through the cable 10 to the monitor for measurement.

The contact pads 75 are connected to the resistors 1001 and 1002 in the same fashion as the monitor connector pins 79-81. Therefore, the manner in which the test current is generated through the contact pads 75 and through the cable 10 is the same as was previously described.

It will be appreciated that although the electrical circuitry shown in FIG. 10 has resistors arranged to produce a test current, many other circuitry arrangements comprised of other, known, electrical components, such as capacitors, inductors, semiconductor devices and voltage sources, can be incorporated in the test plug 70 to provide a suitable test current or other test signal.

Figure 8:
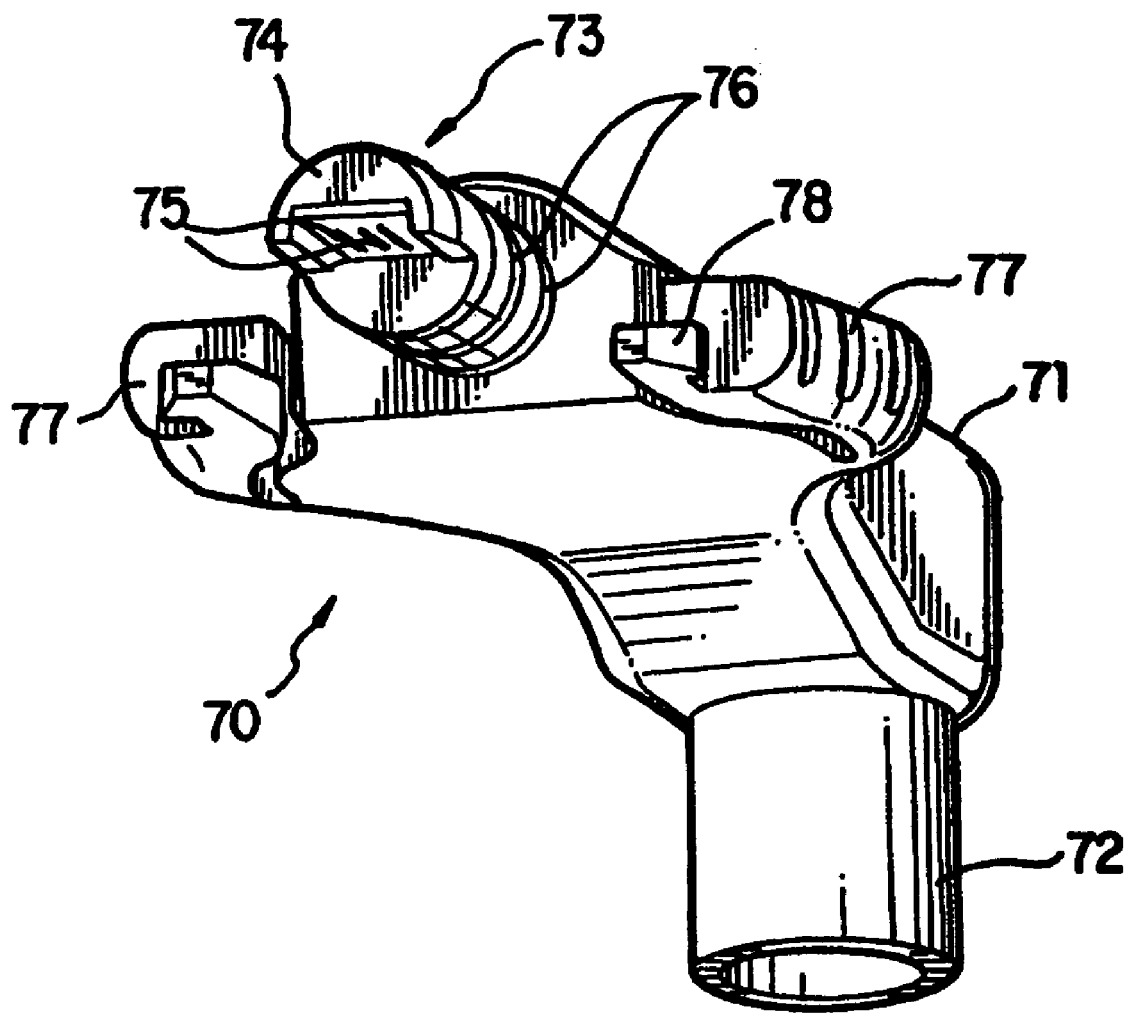
FIG. 8 is a bottom perspective view of the glucose monitoring system test plug of FIG. 7.
Figure 9:
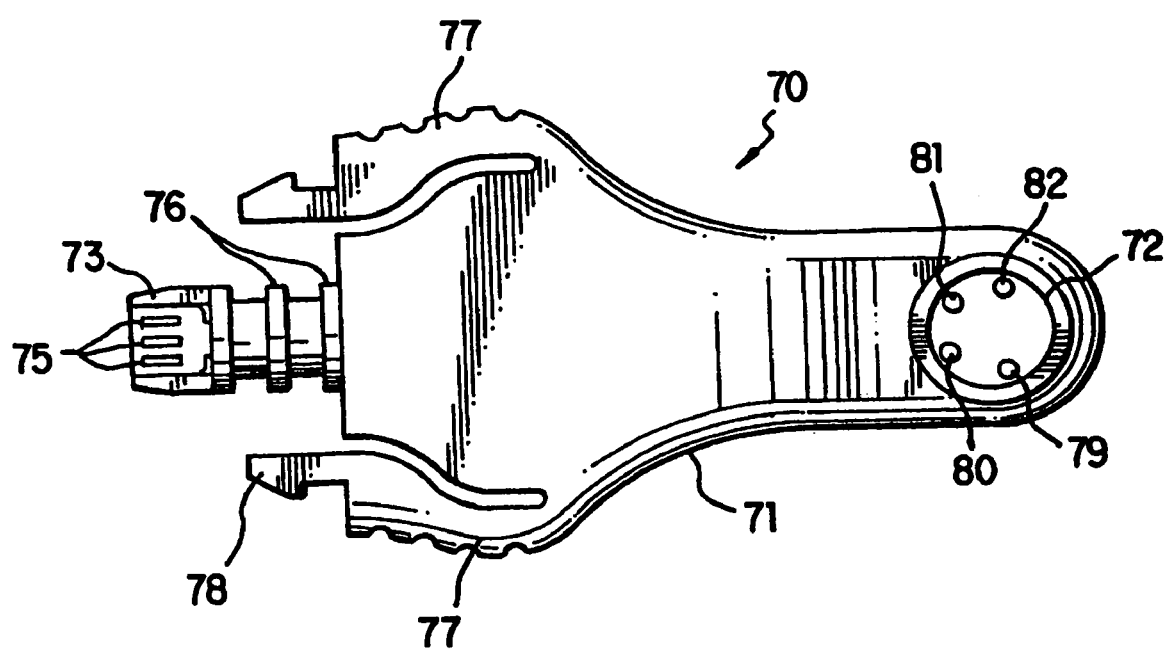
FIG. 9 is a bottom plan view of the glucose monitoring system test plug of FIG. 7.

Referring now to FIGS. 7-9, one embodiment of the test plug 70 of the present invention is shown. The test plug 70 includes a housing 71 which encloses the electrical circuitry, such as that shown in FIG. 10. At one end of the test plug 70 is the monitor connector fitting 72. At the opposite end is the cable fitting 73.

The cable fitting 73 is sized for mating slide-fit engagement with the socket fitting 51 of the cable 10. (FIG. 5) The cable fitting 73 connects to the cable 10 in the same manner as the glucose sensor set 20. Accordingly, the cable fitting 73 is the same as or similar to the sensor fitting 41 and likewise includes a D-shaped fitting key 74 which is received by the cylindrical entry portion 52 of the socket fitting 51. (FIG. 5) The generally D-shaped step portion 53 of the fitting 51 receives the D-shaped fitting key 74 of the cable fitting 73 portion of the test plug 70. (FIG. 7) As shown, the cable fitting 73 includes the plurality of conductive contact pads 75 positioned on the flat portion of the fitting key 74 (FIG. 8) for electrically coupled engagement with the conductive contacts 54 (FIG. 5) of the cable 10. The conductive pads 75 are further coupled to the resistors 1001 and 1002 shown in FIG. 10.

The cable fitting 73 includes positioning rings 76 situated around the tubular portion of the cable fitting 73. Because the insertion set 20 includes seal rings 42 for a seal tight engagement with the socket fitting 51 of the cable 10 (FIG. 4), the positioning rings 76 on the test plug 70 serve as a counterpart to the seal rings 42 and are used to properly center the cable fitting 73 in the socket fitting 51. The D-shaped geometry of the interfitting components 74 and 53 insure proper orientation for correct conductive coupling of the cable 10 to the test plug 70. Although a D-shaped geometry is shown in FIG. 4, other geometries, such as triangles, notches and the like, can be employed to provide proper orientation.

Referring again to FIGS. 5 and 7, the test plug 70 and the sensor connector 12 portion of the cable 10 are retained in releasable coupled relation by interengaging snap fit latch members. As shown, the test plug housing 71 is formed to include a pair of rearwardly projecting cantilevered latch arms 77 which terminate at the rearward ends thereof in respective undercut latch tips 78. The latch arms 77 are sufficiently and naturally resilient for movement relative to the remainder of the housing 71 to permit the latch arms 77 to be squeezed inwardly toward each other.

The permissible range of motion accommodates snap fit engagement of the latch tips 78 into a corresponding pair of latch recesses 55 formed in the sensor connector housing 40 on opposite sides of the socket fitting 51, wherein the latch recesses 55 are lined with latch keepers 56 for engaging the latch tips 78. With this arrangement, the user is able to hear a clicking noise and feel the test plug snap into place. The components can be disengaged for uncoupling when desired by manually squeezing the latch arms 77 inwardly toward each other for release from the latch keepers 56, while axially separating the test plug 70 from the sensor connector 12 portion of the cable 10.

The monitor connector 72 portion of the test plug 70 can be electrically coupled directly to the glucose monitor 21 through the plug receptacle 26 of the monitor 21. (FIG. 2) The monitor connector 72 connects to the glucose monitor 21 in the same manner as the cable 10. The monitor connector 72 has a plurality of pins 79-82 for a snap-in configuration to the glucose monitor 21. (FIG. 9) In this embodiment, the pins 79-81 are used for connection to the test plug resistors 1001 and 1002 as shown in FIG. 10.

Having described the structure of the test plug 70, it can be seen how the test plug 70 can be used to provide diagnostic information that can help indicate if a glucose sensor, the cable or the glucose monitor is operating normally. Referring generally to FIGS. 2 and 7, if the display 28 of the monitor 21 indicates that there is a malfunction, the sensor set 20 can be disconnected from the cable 10. The sensor connector 12 portion of the cable can then be connected to the cable fitting 73 portion of the test plug 70. By pressing the appropriate buttons on the monitor 21, the monitor 21 can apply a test voltage through the cable 10 and the resistors 1001 and 1002 of the test plug 70 and measure the resulting current. The value of the current can be displayed on the monitor screen 28. If the value of the current falls within an acceptable range, then it is known that the monitor 21 and the cable 10 are operating properly. The operational problem therefore likely lies in the sensor set 20 which can be replaced by the user.

On the other hand, if the measured current is outside of the acceptable range of values, then the problem may lie in either the cable 10 or the monitor 21 or both. The user then disconnects the cable 10 from the monitor 21 and from the test plug 70. The monitor connector 72 portion of the test plug 70 may then be connected directly to the plug receptacle 26 of the monitor 21. Once again the appropriate buttons on the monitor 21 are pressed by the user to cause a test voltage to be applied from the monitor 21 directly to the test plug 70 thereby measuring the resulting current. If the value of the current as displayed on the monitor screen 28 falls within an acceptable range, then it may be deduced that the monitor 21 is likely operating properly and that the problem likely lies in the cable 10. The cable 10 can be replaced and the system tested with a new cable to verify proper operation. On the other hand if the value of the current falls outside the acceptable range, then the monitor 21 is likely to have a problem. If the user is unable to locate and correct the monitor 21 problem, the monitor can be sent to a repair facility.

Although shown for use with the cable 10 and the monitor 21, further embodiments of the test plug may be used in telemetered systems to test the various components, such as shown and described in U.S. patent application Ser. No. 09/377,472 and entitled "Telemetered Characteristic Monitor System and Method of Using Same."

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims rather than the foregoing description, and all changes which come within the meaning and range of equivalency of the claims are therefore intended to be embraced therein.

What is claimed is:

1. An electric cable having a proximal end and a distal end, the electric cable for use with a glucose monitor and a glucose sensor and comprising:
   a first connector at the proximal end of the cable;
   a second connector at the distal end of the cable;
   a cable member affixed to the first and the second connectors, the cable member comprising:
      at least one insulated conductor having a gauge number greater than 29 and a strand count greater than 39;
      a conductive shielding layer disposed around the at least one insulated conductor; and
      an insulating layer disposed around the conductive shielding layer, the insulating layer being made of a material selected from the group consisting of USP class VI PVC and thermoplastic elastomer and reinforced elastomer, and wherein the insulating layer has an OD of less than 0.110 inches.

2. The electric cable of claim 1 wherein the insulating layer has nominal thickness of greater than 0.005 inches.

3. The electric cable of claim 1 wherein the at least one insulated conductor has an insulation layer made of a material selected from the group consisting of PVC and polyester.

4. The electric cable of claim 1, further comprising a drain line conductor disposed within the conductive shielding layer, the drain line conductor being adjacent to and in electrical connection with the conductive shielding layer.

* * * * *